Oct. 4, 1932. W. D. BROWNELL ET AL Plant Pat. 28
ROSE
Filed Jan. 19, 1932
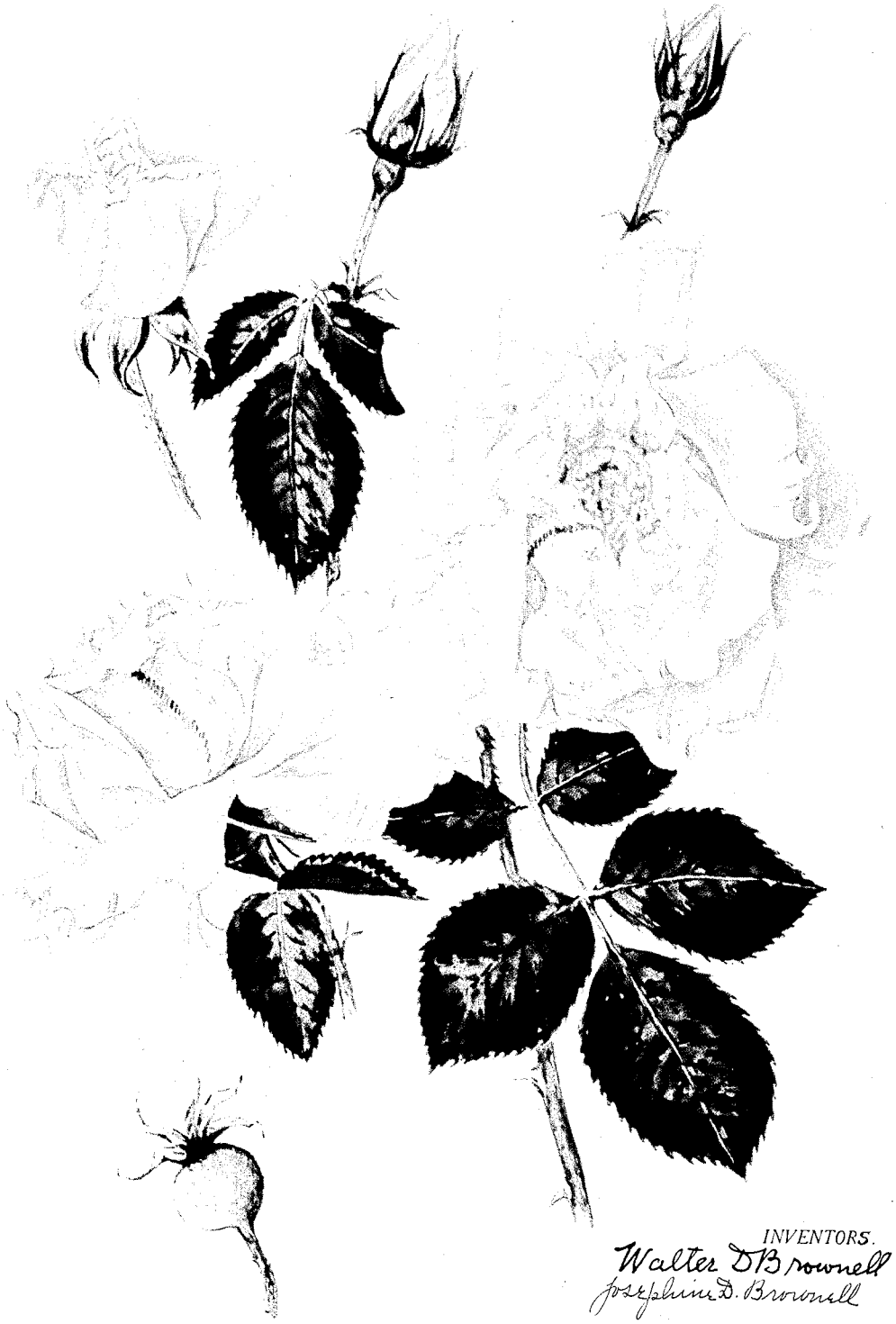
INVENTORS.
Walter D. Brownell
Josephine D. Brownell Patented Oct. 4, 1932

UNITED STATES PATENT OFFICE

WALTER D. BROWNELL AND JOSEPHINE D. BROWNELL, OF PROVIDENCE, RHODE ISLAND

ROSE

Application filed January 19, 1932. Serial No. 587,594.

Our invention relates to roses and especially to a new, original and distinct variety of the class known commercially as "hardy climbing roses", produced by us by cross-breeding, which can be and has been by us asexually reproduced and in which the characteristics thereof are permanently fixed.

Our new rose is new as to the following characteristics and especially as to their joint association in connection with the characteristics of climbing and of hardiness or immunity from serious injury on account of cold temperatures prevailing in certain parts of the northern portion of the United States:

The unique golden yellow color of its petals and their tendency to hold their yellow color under exposure;

The novelty and variation within certain definite limits of the form of the bloom and its large size;

Its special cut-flower value due to its unusually long stem in a hardy climbing rose and its tendency to produce a very limited number of blooms upon each stem, frequently but one;

Its intensity and character of fragrance, and

Its remontant and everblooming habit.

In the accompanying drawing forming a part of this specification we have shown our new rose in its natural colors, that is, as near as is possible to do so artificially.

We otherwise describe our new rose as follows:

Our new rose is a hardy hybrid *Rosa wichuriana*, having been crossed in its ancestral generations with, in addition to *Rosa wichuriana*, several so-called hybrid tea and specie roses.

The characteristics of our new rose are, except as to bud and bloom and blooming characters and except as herein described, substantially similar to the hardy climbing rose known commercially as "Mary Wallace", or more like said rose than any other rose. Our new rose is otherwise described as follows.

Bloom period under comparable conditions begins about three days after the bloom period of "Mary Wallace" begins, attains maximum intensity of bloom about two weeks thereafter then diminishes in intensity of bloom and is everblooming and remontant until winter dormantance.

*Bud:*—Size: Large, usually 1½ to 2 inches in length. Shape: Long, pointed to tapering. Color: Nankin to gold, splashed or striped on outside of outer petal with orange scarlet to blood red, usually of intense brilliance.

*Flower:*—First stages of opening, high centered. Tea to hybrid tea type. Size open usually 4 to 5 inches, often larger.

Petals variable in number usually three to four rows with an inner row of petaloids.

Number averaging around twenty.

Petaloids vary around four.

Petals unfurl from flat to cupped to curled and often wrinkled, with edges plain to irregular to indented to scalloped.

Bloom retains a unique informal to artistic character.

Fragrance, blended, pleasant to sweet, medium to strong. *Rosa wichuriana* and China tea in part.

Color, gold to nearly gold, self, with stamens nankin to nearly nankin, in appropriate light. (Our new rose is described by leading rosarians as more golden yellow than any other rose.) It is particularly noticeable on account of its tendency to retain its color under test of exposure; it, however, fades in the sun to sulphur to nearly sulphur, to lighter on the second and third day of open bloom. Picked in bud and held in the house under normal conditions of display after two days the color of the bloom turns substantially to Maréchal Niel yellow.

Petaloids often stippled with orange scarlet.

Petals fall. Calyx clings.

Borne on stiff stems usually one to two feet long, often longer. Noticeable for its limited number of blooms on stem, very frequently but one bloom on each stem.

*Thorns and prickles:*—New growth nearly blood red to nearly vermillion, fading to a dull weathered color.

*Vigor:*—Very vigorous. Canes grow to fifteen feet or more in one season under favorable conditions.

*Form:*—Climbing, branching. Quantity florescence, especially noticeable in the large number of blooms obtained per plant per season.

*Hips:*—Shape round to nearly round to slightly flat. Size, usually ¾ to ⅞ inches in diameter. Color nearly medium green, turning to orange to russet and blood red and rose madder to brown to dark brown. Sepals attached to hips turn dark brown under sides, upper sides a light green to grey color. Seeds mostly large, woody, hybrid tea type. Number of seeds in mature large hips average around thirteen, average normal hips average around eight seeds.

Our new rose is hardy and resistant to normal winter temperatures and conditions in certain parts of the Northern United States and capable of surviving such winter conditions without serious injury.

We claim:—

The rose as shown and described, characterized by the golden yellow color of its petals, the form and size of its bloom, its stiff long stem, the intense fragrance, and its remontant and everblooming habit.

In testimony whereof we affix our signatures.

WALTER D. BROWNELL.
JOSEPHINE D. BROWNELL.